United States Patent [19]

Fielden et al.

[11] Patent Number: 5,156,814
[45] Date of Patent: Oct. 20, 1992

[54] FLOW INJECTION ANALYSIS

[75] Inventors: Peter R. Fielden, 96 Watling Street, Bury, Lancashire; John R. P. Clarke, Cheadle, both of England

[73] Assignees: University of Manchester Institute of Science & Technology, Manchester; Imperial Chemical Industries PLC, London; Peter R. Fielden, Bury, all of England

[21] Appl. No.: 622,491

[22] Filed: Dec. 3, 1990

Related U.S. Application Data

[62] Division of Ser. No. 384,631, Jul. 20, 1989, abandoned.

[30] Foreign Application Priority Data

Jul. 22, 1988 [GB] United Kingdom ............... 8817456

[51] Int. Cl.$^5$ ................ G01N 33/50; G01N 33/96
[52] U.S. Cl. ...................................... 422/108; 422/81; 422/110; 422/112; 73/864.81; 73/61.56; 137/209; 137/212; 137/624.15; 417/18; 417/118; 417/120
[58] Field of Search ............... 422/57, 62, 63, 67, 422/68.1, 81, 82.13, 108, 110, 111, 112; 436/34, 52, 53; 73/61.1 C, 863.71, 864.81; 137/501, 510, 209, 212, 624.15; 417/118, 18, 120

[56] References Cited

U.S. PATENT DOCUMENTS

| 3,749,113 | 7/1973 | Isreeli et al. | 137/209 |
| 4,567,748 | 2/1986 | Klass et al. | 422/68.1 |
| 4,683,212 | 7/1987 | Uffenheimer | 436/52 |
| 4,740,356 | 4/1988 | Huber | 422/81 |
| 4,865,811 | 9/1989 | Newton et al. | 422/81 |
| 5,098,657 | 3/1992 | Blackford | 422/73 |

Primary Examiner—James C. Housel
Assistant Examiner—David Redding
Attorney, Agent, or Firm—Charles E. Baxley

[57] ABSTRACT

A liquid pump, particularly though not exclusively suitable for use in flow injection analysis, and comprising a reservoir 3 an outlet tube 6 for conducting liquid 2 from the reservoir and a device for introducing gas into the liquid in the reservoir to displace liquid therefrom through the tube. The gas may be introduced in the form of a series of rapid pulses of controlled duration and frequency and is introduced at a fixed level relative to the entrance to the outlet tube.

10 Claims, 5 Drawing Sheets

FLOW INJECTION ANALYSIS

This is a continuation of application Ser. No. 384,631 filed Jul. 20, 1989, now abandoned.

This invention relates to flow injection analysis and particularly to an improved flow injection analysis system having the capability of performing analysis with improved precision and repeatability and being programmable for control by a computer. A particular feature of the system is a novel sample preparation pump which is useful in applications other than flow injection analysis, for example calibration, optimization and detector characterization and as part of a small-scale reactor system.

Flow injection analysis (FIA) is a versatile technique available to the analyst for carrying out analyses of fluids, especially liquids. In essence, the technique comprises mixing a sample of a fluid to be analysed with one or more reagents which react with the sample in a carrier whilst travelling to a detector which responds to any changes induced by the reaction. The system may be operated by injecting a sample into a carrier stream containing the reactant(s) (normal FIA) or by injecting reactant(s) into a carrier stream containing the sample (inverse FIA). The system permits accurate control over the time interval between injection of the sample or reagent and the detector, thereby allowing reaction products to be detected without waiting for a steady-state to be reached, so allowing rapid sampling and enabling reactions to be used which do not go to completion in the permitted time interval before detection. A typical instrument for carrying out FIA comprises a pump for pumping the carrier, a sample injector, optionally a coil providing the required residence time for reaction and a detector.

Known forms of pump for these purposes include peristaltic pumps and bottle-like reservoirs from which liquid is displaced by introducing gas under pressure to the ullage therein from a gas source by way of a regulator valve. Such regulator valves are not particularly accurate and do nothing to compensate for the changing head of liquid in the reservoir above the liquid outlet.

The present invention resides in the discovery that improved results are obtained in FIA systems by providing a steadier flow of fluid than is obtainable using previously used pumps. The improved fluid handling system is reliable and can be (and preferably is) made even more reliable and precise by being designed for use with computer control giving flexibly programmable apparatus.

According to one aspect of the invention there is provided a liquid pump comprising a reservoir, an outlet tube for conducting liquid from the reservoir and means for introducing gas into the reservoir to displace liquid therefrom through said tube, characterized in that the gas is fed into the liquid in the reservoir.

The gas may be fed into the liquid at a fixed level therein relative to the entrance to the outlet tube and such as to maintain a constant pressure at that level.

The gas may be introduced above ambient pressure, or drawn in by suction applied to the outlet tube.

The fixed level may be at or adjacent said entrance.

In this way, the pressure in the liquid expelled from the bottle remains constant, thereby ensuring that the liquid flow is constant.

The pressurizing gas may be fed into the reservoir in the form of a series of precisely controlled rapid pulses of gas. The pulse duration may be variable depending upon the desired rate of flow of liquid; by way of example the pulse duration may be say 2 milliseconds for a low liquid flow rate and up to 20 milliseconds for a high liquid flow rate. It will be appreciated that these figures relate to standard type FIA devices and may be different for another size of device. The pulse repetition frequency may be controllable up to about 200 Hz but in general will be set at a maximum of about 20 Hz in order to conserve valve lifetime.

Thus pulse duration and pulse repetition frequency may be controlled thereby providing control of solvent-/reagent flow rates and amount of solvent/reagent delivered. In a standard device, flow rates of up to about 5 ml/minute are typical; higher flow rates are possible using reservoirs designed to withstand higher internal pressures.

The pressure of the gas at the end of the gas inlet tube can be sensed, optionally in a computer-controlled device, and compared with a reference signal (e.g. computer generated) which is related to atmospheric pressure. Pressure sensing may be, for example, by a piezo-resistive differential pressure sensor. Any difference between the measured pressure and the reference signal is used to vary the gas flow rate by changing either or both of the pulse duration and the pulse repetition frequency, these being changed by alteration of the timing of the gas release valve. Using this pressure control technique, the pressure difference between the drive gas and the ambient atmosphere is maintained regardless of any fluctuations in ambient pressure (and, within reason, gas pressure) and/or solvent/reagent demand. This constancy of pressure difference is especially valuable in cases where a valve is introduced after the pump to stop or switch the liquid flow.

As indicated above, the device can be operated at high or low solvent/reagent flow rates. In the case of low solvent/reagent flow rates in particular a gas bleed may be provided in the system. A gas bleed line may be connected to the head space to permit a slow escape of gas from the head and ensure better control of the drive gas pressure and hence the liquid flow rate.

The system is not restricted to a single sample or reagent pump and indeed several pumps, each of the improved design described hereinbefore, may be provided. The system thus has the capability of mixing a single sample with one or several reagents, several samples with a single reagent or more than one sample with more than one reagent.

The improved FIA system of the invention affords a number of advantages over the conventional system using prior known pumps. The system provides a pulse-less, jitter-free delivery of solvent/reagent at a smooth, controlled flow rate. There is no backlash at start/stop of liquid flow downstream of the solvent/reagent pump(s) and an instant start is achieved in stopped-flow experiments. Since the pressurizing gas is introduced into the body of the solvent/reagent it serves to purge or de-gas the solvent/reagent as it rises to the head space, thereby avoiding air bubbles in the solvent/reagent. For effective purging and/or de-gassing of the liquid, we have used helium with good results. The pump system and indeed the entire device can be constructed of materials which are inert to the solvent and/or the reagent so that the need for replacement of consumable parts (such as the elastomer tubing of peristaltic pumps) is obviated.

The system affords an active feedback control of the pressure head in the pump and a high tolerance of changes in ambient pressure and drive gas pressure. The system compensates for changes in the liquid (solvent-/reagent) level in the pump as solvent/reagent is consumed, thereby obviating the need for maintaining a constant liquid level. There is no need for high quality gas regulators, although a good quality low pressure relief valve followed by a capillary restrictor is advisable for safety. The pump can deliver very low solvent-/reagent flow rates reproducibly and precisely.

The detector of the FIA system may be any of those usually used in FIA devices, for example a spectrophotometer, a liquid chromatograph, an electrochemical sensor or an atomic spectroscope.

The liquid pump may be used with an FIA manifold including a sampling section comprising a length of line between valve means at its opposite ends, the valve means being operable first to enable the filling of said length with sample and second its expulsion into a carrier stream.

The FIA manifold may include a line for carrying one fluid via valve means for mixing with another fluid flowing through another line, there being means to open and close the valve means repeatedly at high frequency to ensure rapid intimate mixing of the two fluids.

BRIEF DESCRIPTION OF DRAWINGS

The invention will now be illustrated by way of example only with reference to the accompanying drawings, in which.

Figure 1:
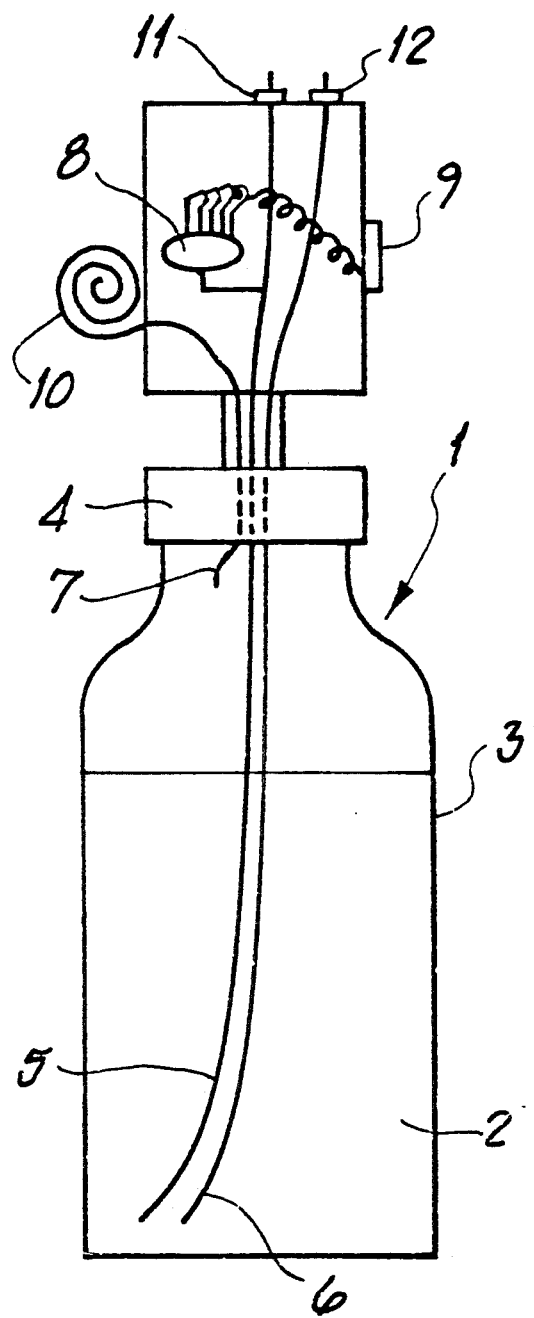
FIG. 1 shows a solvent/reagent pump.

Referring first to FIG. 1, a pump 1 for delivering a liquid 2 (a solvent or reagent, for instance) into a carrier stream comprises a reservoir in the form of a bottle 3 fitted with a screw-cap 4 through which pass tubes 5 and 6. Tube 5 provides an inlet for a gas and tube 6 provides an outlet for the liquid 2. Both of the tubes 5 and 6 open near the bottom of bottle 1 and the open end of each is at the same level beneath the surface of the liquid.

Although in the pump shown in FIG. 1 the gas inlet tube 5 and the liquid outlet tube 6 open at the same level in the liquid, it will be appreciated that this is only a preferred design and that the opening of the tubes may be at different levels within the liquid provided that the difference in levels remains constant.

A capillary tube 7 also passes through the cap 4 and is connected to a capillary tube 10 (shown coiled but not necessarily coiled) open at its free end to provide a bleed line for the gas in the head space.

The gas inlet tube 5 has a side arm which connects it with a pressure sensor 8 which is wired to a terminal 9 for connecting the sensor to the pump control circuit. Gas inlet tube 5 is provided with a connector 11 for connecting the tube to a drive gas control valve (optionally computer-controlled). Liquid outlet tube 6 has a connector 12 for connecting it through a valve (optionally computer-controlled) to a FIA manifold.

Figure 2:
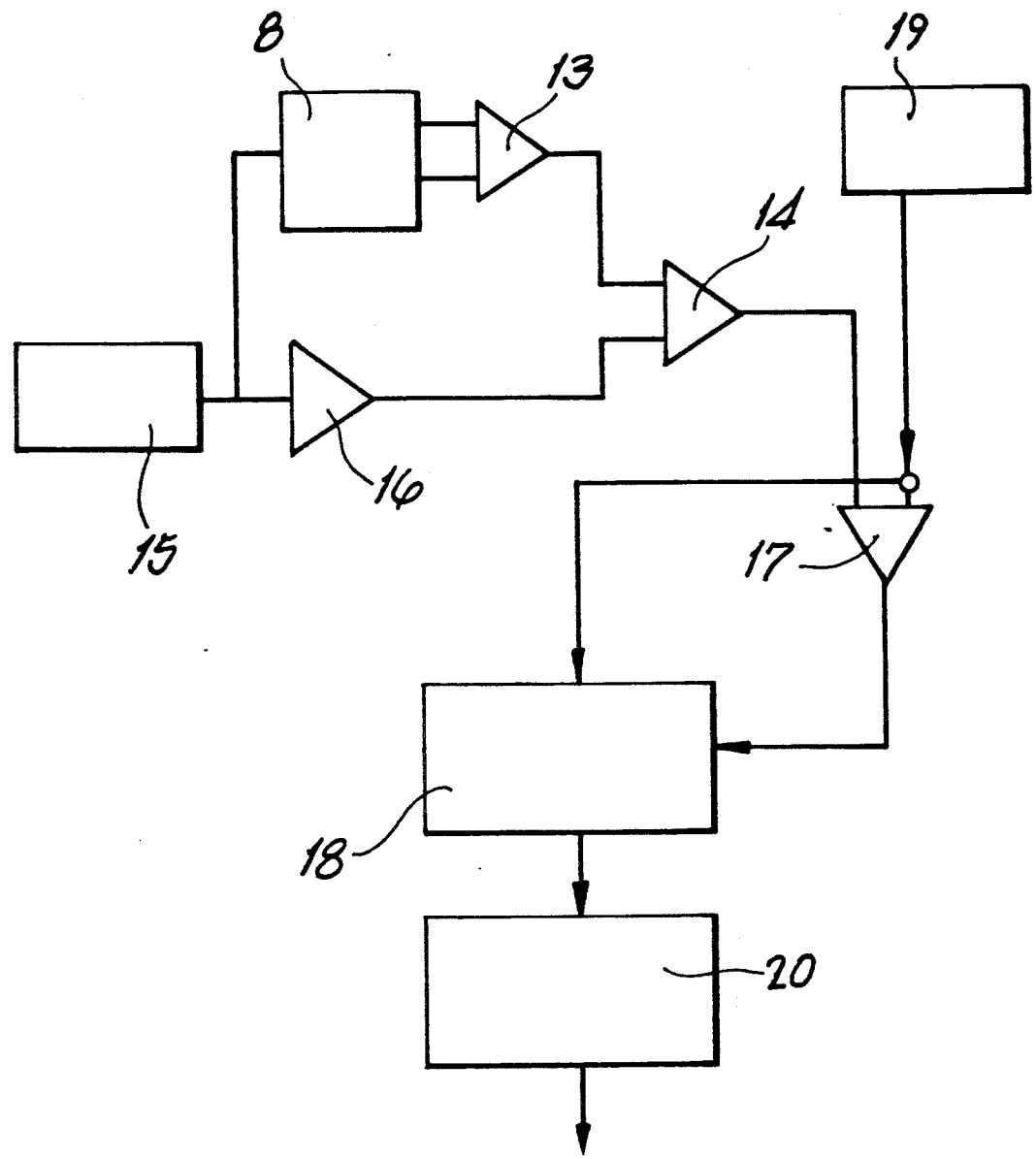
FIG. 2 shows a schematic representation of a control circuit for the pump of FIG. 1.

FIG. 2 shows schematically a control circuit for inlet of drive gas to the pump. The signal from pressure sensor 8 (preferably referenced to atmospheric pressure) is amplified at 13 and passed to a differential amplifier 14 together with a reference voltage signal from 15 amplified at 16. It will be appreciated that various electronic configurations may be utilised to enhance the stability of the reference signal. In the embodiment shown in FIG. 2, the amplified signal from 14 is passed through a comparator 17 to a digital pulse generator 18 where together with a further signal (optionally computer generated) from 19 it controls the frequency and duration of pulse generation in accordance with the requirement to control the gas inlet pressure. For example a computer generated signal may not only control pulse duration but may also establish a voltage set point to which the pressure transducer is compared by comparator 17 in order to define the required pressure of the inlet gas. Controlled in this way, the signal from pulse generator 18 passes to a valve-driver 20 a signal containing information as to the pulse duration and pulse repetition needed to maintain or establish a desired condition within the pump.

Figure 3:
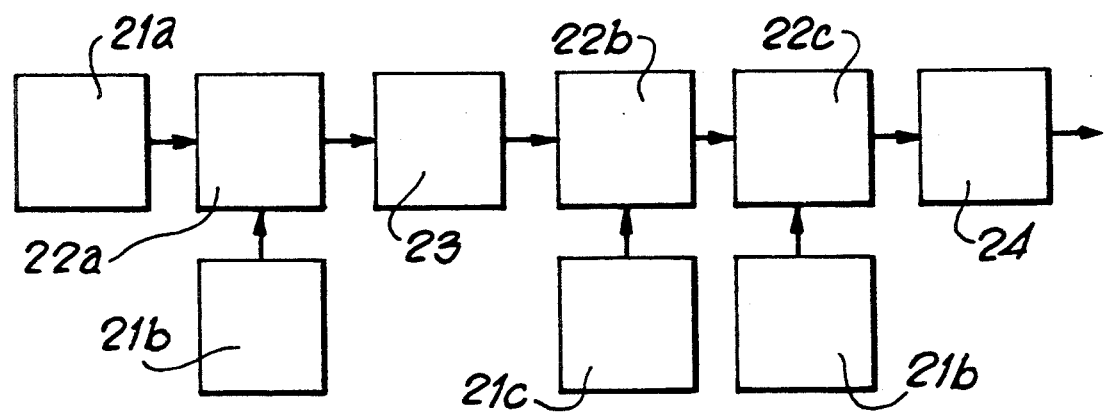
FIG. 3 is a schematic representation of an FIA manifold in which each element of the system is under the control of a computer.

A FIA manifold comprising pumps as shown in FIG. 1 is illustrated in FIG. 3, in which 21a, 21b, 21c and 21d are solvent/reagent pumps, 22a, 22b and 22c are mixers, for example three-way valves, and 23 is a sampling system (described with reference to FIG. 4). A detector 24, for example a spectrophotometer, connects with the manifold. As will be apparent, in principle the manifold enables any number of solvent/reagent liquids to be mixed in any desired proportions with a sample or samples. Each of the solvent/reagent pumps is designed and controlled as described above to deliver a precise amount of liquid.

Figure 4:
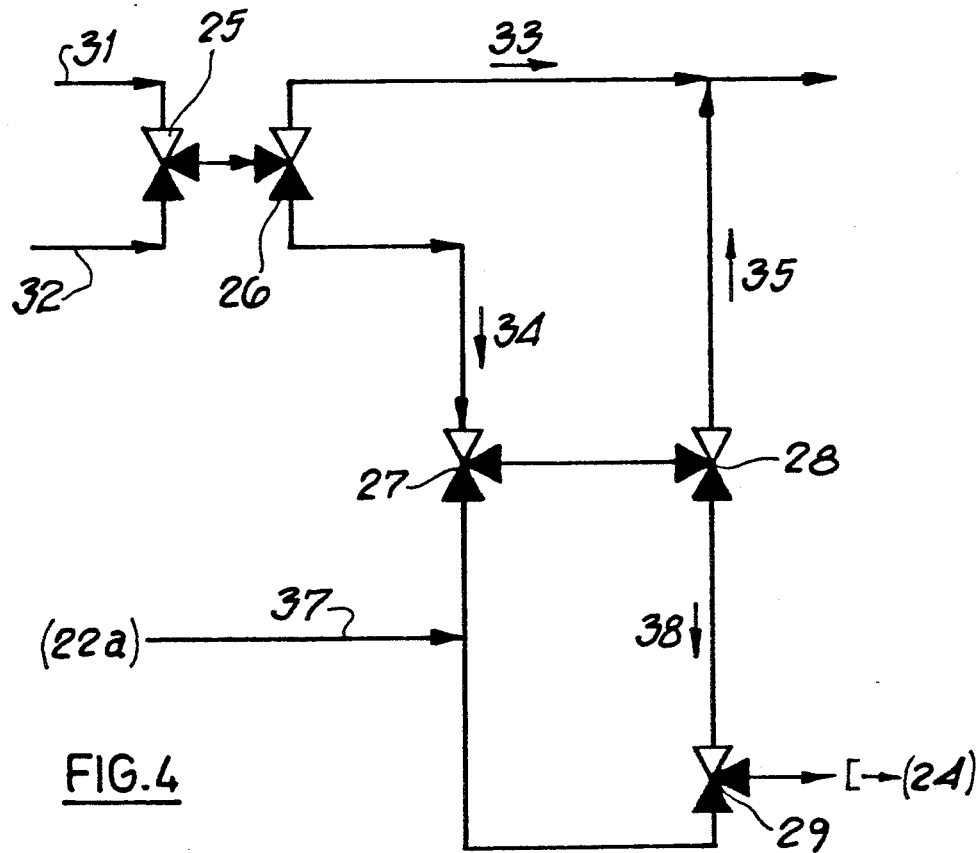
FIG. 4 is a schematic representation of a system of three-way valves in one example of a sampling arrangement.

The sampling system 23 is shown schematically in FIG. 4 and consists of five interconnected three-way valves 25 to 29. Valve 25 is connected by line 31 with a source of a wash fluid and through line 32 with a source of a sample of the material to be analysed. Valve 25 is switchable to pass either the wash fluid or the sample to a second valve 26 which again is a three-way valve. Valve 26 enables wash fluid to be passed directly to drain or waste disposal in the direction of arrow 33 or sample to be passed towards the manifold system in the direction of arrow 34. Three-way valve 27 switches either the sample received from valve 26 or a (carrier) stream from line 37 to valve 28. At valve 28 the sample can be switched either to the waste disposal line (arrow 35) or to the detector [arrow 38—via a valve 29 and mixers 22b and 22c (FIG. 4)]. Valve 29 completes the sampling system and as shown enables a (carrier) stream from line 37 to pass directly to the detector (via mixers 22b and 22c) or the (carrier) stream can be switched into the sample line via valve 27.

Operation of the sampling system is as follows. For stopped-flow sampling, i.e. where the flow of fluid to the detector is intermittent, valves 25 and 26 are operated to allow sample to flow to line 34 and valves 27 and 28 allow flow to line 35. Valve 29 prevents flow of carrier to the detector. In this arrangement, sample passes through valves 25, 26, 27 and 28 to waste and the flow of carrier fluid is cut off. Valve 28 is operated to allow sample to pass to valve 29 and the detector line and at the same time valve 27 is operated to stop the flow of sample from line 34 and pass a (carrier) stream from line 37 so that carrier drives the sample located between valves 27 and 28 to the detector line via valve 29. Thus slugs of sample can be passed to the detector.

For continuous-flow sampling, i.e. where there is a continuous flow of fluid to the detector, sample flows through valves 25, 26, 27 and 28 to waste, whilst carrier fluid flows through valve 29 to the detector line. If at the same time valves 27, 28 and 29 are switched then the sample flow from line 34 is cut off and a slug of sample (i.e. that located between valves 27 and 28) is driven through the detector line by carrier fluid. Thus, there is a continuous flow of fluid through the detector line whilst slugs of sample are entrained as desired.

To purge the system of sample, valves 25 and 26 may be operated to purge the sample directly to waste, whilst valves 27 and 28 allow carrier fluid to pass either to waste or to the detector line.

To wash out the sampling system, valves 25, 26, 27 and 28 are operated to allow washing fluid to pass through the lines between valves 26, 27 and 28 to waste or to the detector via valve 29.

It will be appreciated that the various valve change sequences to perform the various operational functions can be programmed into a computer so that a predetermined program of analyses can be carried out automatically.

In the manifold system described with reference to FIGS. 3 and 4 the fluids (wash, sample, carrier or reagent fluids) are driven through under positive drive gas pressure but it will be appreciated that instead the fluids may be drawn through the system by reduced pressure. A system of the latter type may comprise, for example, a manifold system as shown in FIG. 3 having a pressure reduction unit connected after the detector 24, a suitable pressure reduction unit being illustrated in FIG. 5.

Figure 5:
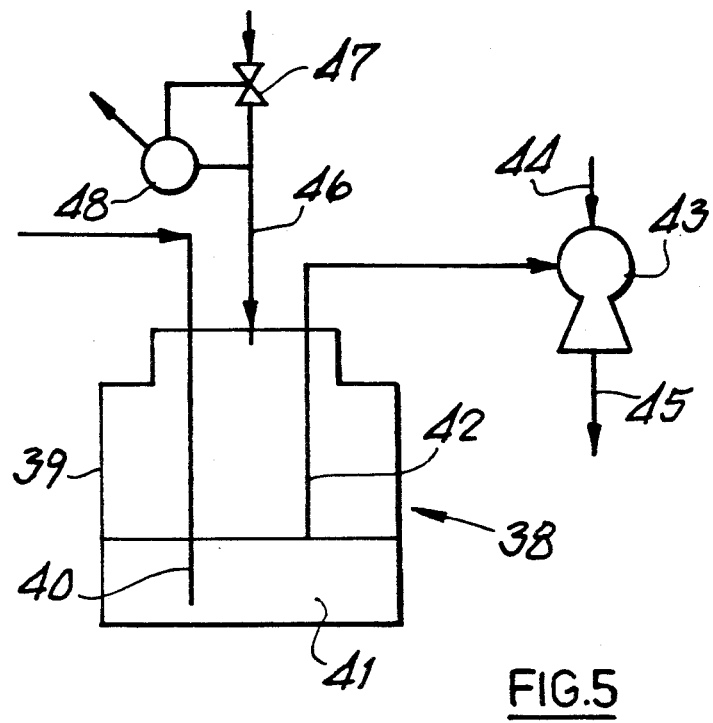
FIG. 5 shows a pressure reduction unit suitable for drawing fluids through the manifold system shown in FIG. 3, FIGS. 6a, 6b and 6c show three types of mixers which can be used in the manifold system of FIG. 3.

Referring to FIG. 5, the pressure reduction unit or vacuum control unit 38 comprises a pressure rated vessel 39 into which waste fluid from the detector (24) is drawn through line 40 into a constant head of liquid 41. A line 42 connects vessel 39 to an ejector device 43 in which the flow of a gas or liquid via inlet 44 and outlet 45 (to drain, for instance) creates a suction on line 42 and draws fluid from vessel 39. The reduced pressure thereby created in vessel 39 in turn draws fluid from the detector through line 40 and in fact draws fluid through the entire manifold system. The magnitude of the reduced pressure effected in this way is controlled by allowing the controlled influx of gas, e.g. ambient air, into vessel 39 through a line 46 via a control valve 47 such as a three-way valve of the fail-to-open type. Valve 47 is controlled in the same way as is described hereinbefore for the positive pressure drive gas valves of the pump shown in FIG. 1. A pressure sensor/control unit 48 monitors the reduced pressure relative to that of the gas source (ambient) and releases pulses of gas into vessel 39 using a control circuit similar to that illustrated in FIG. 2.

As described, the reduced pressure unit may be located after the detector 24 in the manifold system of FIG. 3 so as to draw fluids through that manifold instead of driving the fluids through using a pressurised gas source. Alternatively, the reduced pressure unit can advantageously be added to the manifold system to supplement rather than replace the positive drive facility. In this way, a greater pressure differential can be provided across the manifold without exceeding the pressure rating of the pressurised vessels. Thus, for instance, a faster throughput of fluids may be achieved and the system is better equipped to handle viscous fluids which may be encountered as samples and/or reagents.

It will be appreciated that in the manifold equipped with a reduced pressure unit, the sample and/or reagent pumps may be simpler devices operating on the mariot principle. It will be appreciated also that in the draw-through system there is no requirement for a pressurized gas source; this makes the system more attractive for transport for field uses, for example.

Figures 6A, 6B, 6C:
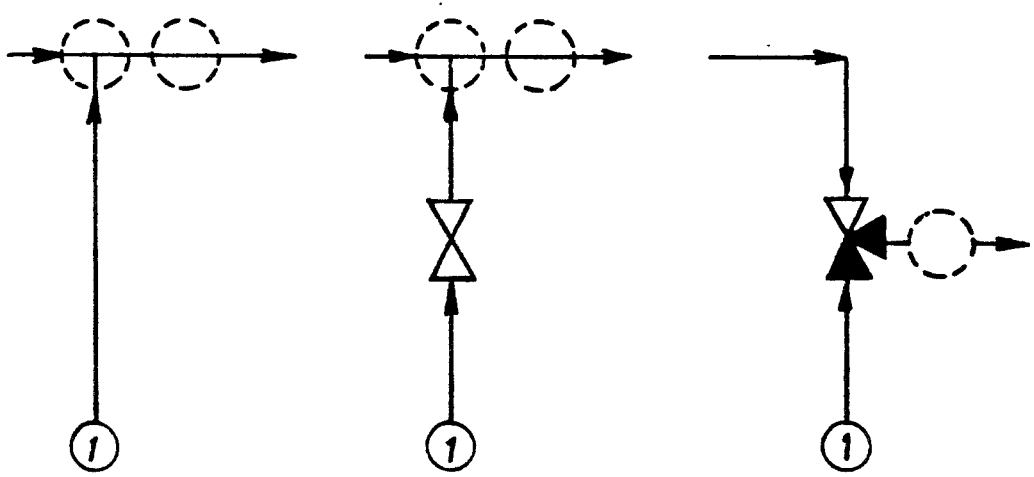

The manifold system shown in and described with reference to FIG. 3 comprises mixers 22a, 22b and 22c and three types of mixers which may be utilised are represented as FIGS. 6a, 6b and 6c in FIG. 6. In FIG. 6 the member denoted as 1 is a pump essentially as shown in FIG. 1.

The device shown in FIG. 6a is for continuous delivery of one fluid (from the pump) into another fluid stream. Thus with reference to FIG. 3 any of the mixers 22a, 22b and 22c may have this configuration. If desired, further mixers may be provided as shown in broken lines in the drawing.

FIG. 6b shows a mixer comprising a two-way valve which allows intermittent addition of one fluid (from the pump) into another fluid stream. Pulse-free delivery of fluid from the pump and repeated operation at high frequency (typically 1 Hz-100 Hz) of the two-way ratioing valve ensures effective mixing of the two fluid streams. The valve may be operated with any desired mark space ratio. Optional additional mixers may be provided as shown in broken lines in the drawing.

The ratioing valve is preferably a low dead-volume three-way valve such as is shown in FIG. 6c. An optional additional mixer may be provided as shown in broken lines in the drawing.

In the arrangement of FIG. 6a the fluid mixing ratio is determined solely by the relative pressures of the fluid streams being mixed. In the arrangements shown in FIGS. 6b and 6c, however, the valve introduces a further control over the mixing ratio since in this case the valve timing as well as the fluid pressure influences delivery of the fluid.

Irrespective of the type of mixing device employed it is preferred that the mixing operation at each point in the manifold system can be controlled by computer in order to ensure precise and repeatable blending of fluid streams even when sampling procedures are undertaken.

Figure 7:
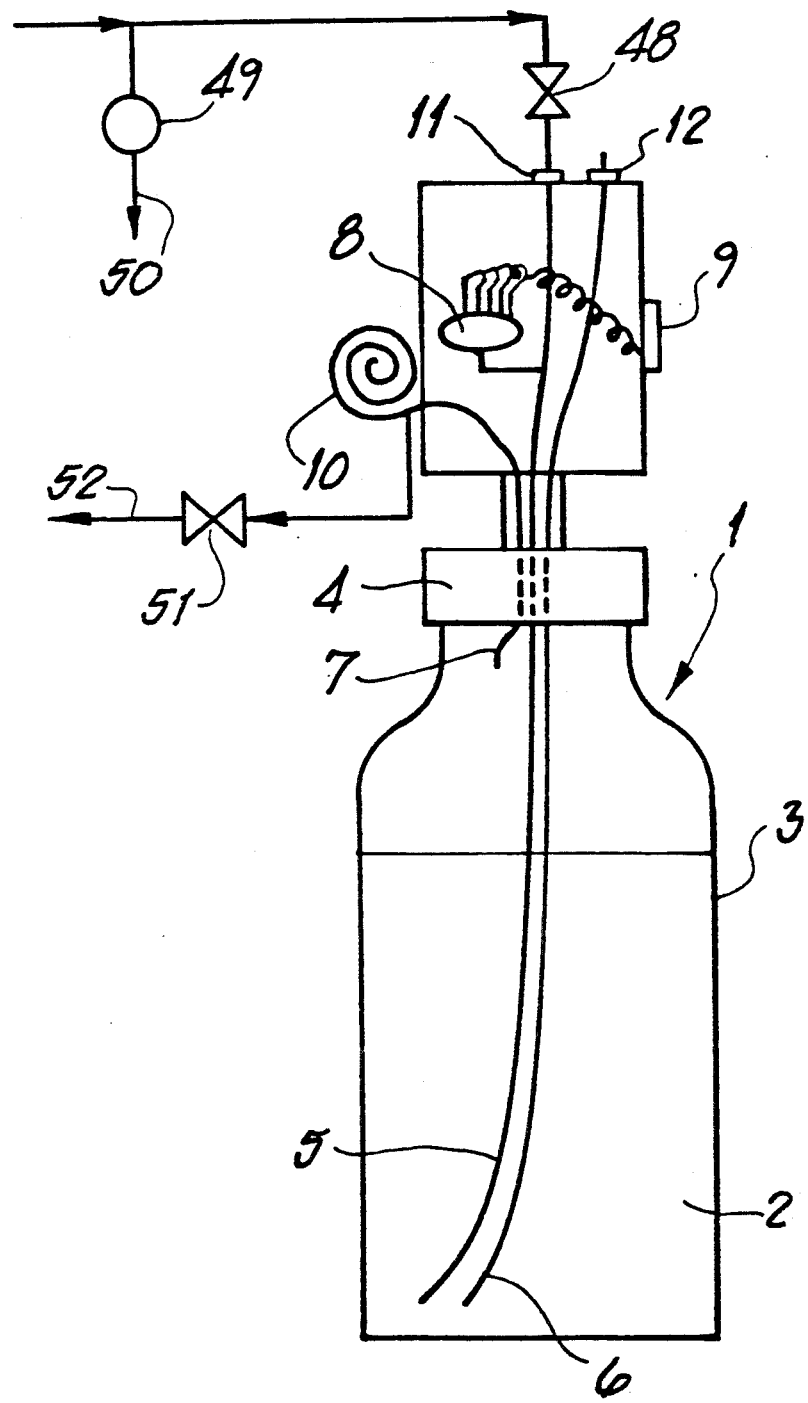
FIG. 7 shows the pump of FIG. 1 provided with various safety features.

Some safety features which it is desirable to build into the pump and its control system are illustrated in FIG. 7. As shown in this Figure, the system is modified by incorporation of an additional pressure sensor and a pressure relief valve. The gas inlet tube 5 is connected to a gas inlet valve 48 in advance of which is provided a side arm to a pressure sensor 49. The signal 50 from pressure sensor 49 is compared with the signal from pressure sensor 8. The pressure sensed at sensor 49 should always be greater than that sensed at sensor 8. The gas bleed tube 7 is connected through a relief valve 51 to a vent line 52.

These features are designed to cater for situations where there is a failure of the gas supply which otherwise could result in damage due to the drawing of liquid from the pump back into the pressure sensor 8 or even into the gas supply valve 48 and the source of the gas. In the modified system of FIG. 7, in the event of a failure of the gas supply or of it being inadvertently turned off, the gas pressure in the headspace of the pump exceeds that in the gas supply through valve 48. The pressure sensor 49 measures the pressure of the gas supply to valve 48 and compares it with the headspace pressure measured by sensor 8. A dedicated electronic circuit controls the relief valve 51 such that it is opened thereby venting the headspace within the pump. The system can be set up so that further operation of the pump is halted until the fault has been corrected and the valve 51 has been reset. In the event of a power failure, gas supply valve 48 is closed to shut off the gas source and valve 51 is opened to vent the pump headspace.

Other safety features (not illustrated) which are desirable are a pressure relief valve (say 10 psig-68 kPa) in the gas supply line and a capillary restrictor in the gas supply line. Also it is advisable to employ a pump body, e.g. a plastic-coated glass bottle or a plastic bottle, designed to withstand a much greater internal pressure than is ever likely to be encountered in normal usage of the pump.

We claim:

1. A liquid pump comprising a reservoir, an outlet tube for conducting liquid from said reservoir and an inlet tube for introducing gas into the liquid in said reservoir to displace liquid therefrom through said outlet tube, means for producing an electrical output signal which varies in dependence upon the pressure head in said pump and making a comparison between said output signal and an electrical reference signal and means for utilizing the comparison to control the feed of gas through said inlet tube into said reservoir.

2. A liquid pump according to claim 1, further comprising means for introducing gas into said reservoir in the form of a series of pulses controlled by said utilizing means.

3. A liquid pump according to claim 1, further comprising means for feeding gas into the liquid from said inlet tube at a fixed level therein relative to an entrance to said outlet tube and such as to maintain a constant gas pressure at said fixed level.

4. A liquid pump according to claim 3, wherein the fixed level is at or adjacent said entrance to the outlet tube.

5. A liquid pump according to claim 1, further comprising means for introducing gas into said reservoir at a pressure above ambient pressure.

6. A liquid pump according to claim 1, further comprising means for introducing gas into said reservoir by the application of suction to said outlet tube.

7. A liquid pump according to claim 1, including a gas bleed line from a location above the liquid in said reservoir.

8. A liquid pump comprising a reservoir, an outlet tube for conducting liquid from the reservoir and an inlet tube for introducing gas into the liquid in said reservoir to displace liquid therefrom through said outlet tube, means for producing an electrical output signal which varies in dependence upon the pressure head in said pump and making a comparison between said output signal and an electrical reference signal, means for utilizing the comparison to control the feed of gas through said inlet tube into said reservoir, and means for introducing gas into said reservoir in the form of a series of pulses controlled by said utilizing means.

9. A liquid pump according to claim 8, wherein said pulses are of fixed frequency and variable duration.

10. A liquid pump according to claim 8, wherein said pulses are of fixed duration and variable frequency.

* * * * *